(12) United States Patent
Dehne et al.

(10) Patent No.: US 6,245,772 B1
(45) Date of Patent: Jun. 12, 2001

(54) FUNGICIDAL ACTIVE COMPOUND COMBINATIONS

(75) Inventors: Heinz-Wilhelm Dehne, Monheim; Wilhelm Brandes, Leichlingen; Karl-Heinz Kuck; Thomas Seitz, both of Langenfeld, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/541,922

(22) Filed: Apr. 3, 2000

Related U.S. Application Data

(62) Division of application No. 09/110,528, filed on Jul. 6, 1998, now Pat. No. 6,057,363, which is a division of application No. 08/802,157, filed on Feb. 19, 1997, now Pat. No. 5,776,976, which is a division of application No. 08/554,142, filed on Nov. 6, 1995, now Pat. No. 5,650,423, which is a division of application No. 08/192,333, filed on Feb. 4, 1994, now Pat. No. 5,491,165.

(30) Foreign Application Priority Data

Feb. 12, 1993 (DE) .................................................. 43 04 172

(51) Int. Cl.$^7$ .............................. A01N 43/54; A01N 47/10
(52) U.S. Cl. ......................... 514/269; 514/478; 514/479
(58) Field of Search .................................. 514/269, 478, 514/479

(56) References Cited

U.S. PATENT DOCUMENTS 5,453,531 * 9/1995 Seitz et al. .............................. 560/29

FOREIGN PATENT DOCUMENTS

| 472996 | 8/1991 | (EP) . |
| 493683 | 11/1991 | (EP) . |
| 550788 | 1/1992 | (EP) . |

OTHER PUBLICATIONS

Brighton Crop Protection Conference (1992) 5–6, 435–37.*

* cited by examiner

Primary Examiner—Allen J. Robinson
(74) Attorney, Agent, or Firm—Norris McLaughlin & Marcus

(57) ABSTRACT

New active compound combinations of valinamide derivatives of the formula (I)

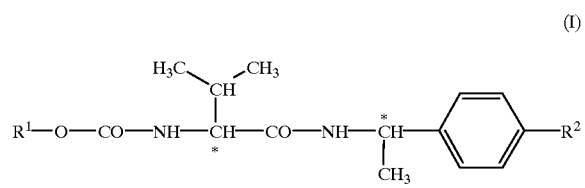

in which $R^1$ and $R^2$ has the meaning given in the description, with known fungicidal active substances, and their use for combating phytopathogenic fungi are described.

2 Claims, No Drawings

FUNGICIDAL ACTIVE COMPOUND COMBINATIONS

This application is a division of Application Ser. No. 09/110,528, filed Jul. 6, 1998 (now U.S. Pat. No. 6,057,363); which is a division of U.S. Ser. No. 08/802,157, filed Feb. 19, 1997 (now U.S. Pat. No. 5,776,976); which is a division of U.S. Ser. No. 08/554,142, filed Nov. 6, 1995 (now U.S. Pat. No. 5,650,423); which is a divsion of U.S. Ser. No. 08/192,333, filed Feb. 4, 1994 (now U.S. Pat. No. 5,491,165).

The present application relates to new active compound combinations composed of, on the one hand, valinamide derivatives and, on the other hand, of other, known fungicidal active compounds, and which are highly suitable for combating phytopathogenic fungi.

It is already known that valinamide derivatives has fungicidal properties (cf. EP-A 472,996). The activity of this substance is good; however, it leaves something to be desired in some cases when low application rates are used.

Furthermore, it is already known that a large number of azole derivatives, aromatic carboxylic acid derivatives, morpholine compounds and other heterocycles can be employed for combating fungi (cf. K. H. Büchel "Pflanzenschutz und Schädlingsbekämpfung" [Crop Protection and Pest Control] pages 87, 136, 140, 141 and 146 to 153, Georg Thieme Verlag, Stuttgart 1977). However, the activity of the substances in question is not always satisfactory when low application rates are used.

It has now been found that the new active compound combinations of valinamide derivatives of the general formula (I)

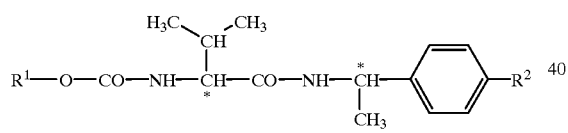

in which $R^1$ represents i-propyl or s-butyl and $R^2$ represents chlorine, methyl, ethyl or methoxy, and (A) dichlofluanid, of the formula (II)

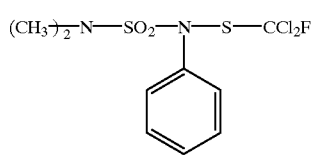

and/or (B) tolyifluanid, of the formula (III)

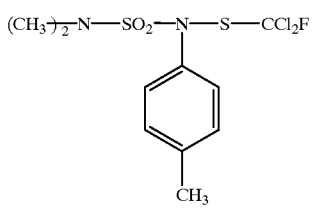

and/or (C) tetrachloro-isophthalo-nitrile of the formula (IV)

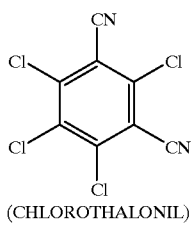

(CHLOROTHALONIL)

and/or (D) propineb, of the formula (V)

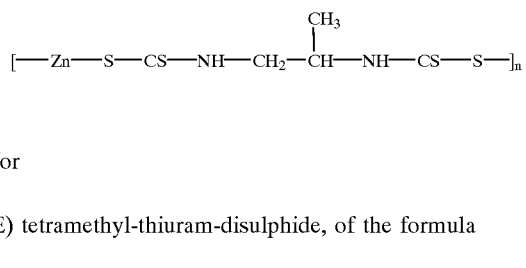

and/or (E) tetramethyl-thiuram-disulphide, of the formula (VI)

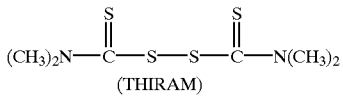

(THIRAM)

and/or (F) mancozeb, of the formula (VI)

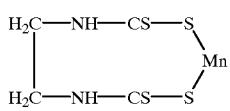

and/or (G) dyrene, of the formula (VII)

[chemical structure: phenyl-NH-triazine-2,4-dichloro]

and/or (H) copper oxychloride and/or (I) captan of the formula (VIII)

[chemical structure: tetrahydrophthalimide-N-S-CCl₃]

and/or (K) a morpholine derivative of the formula (IX)

[chemical structure of Dimetomorph: 4-chlorophenyl, 3,4-dimethoxyphenyl, C=CH-CO-morpholine]

(Dimetomorph)

and/or (L) dithianon, of the formula (X)

[chemical structure of dithianon]

and/or (M) Phaltan, of the formula (XI)

[chemical structure: phthalimide-N-S-CCl₃]

and/or (N) cymoxanil, of the formula (XII)

$$CH_3-CH_2-NH-\overset{O}{\underset{}{C}}-NH-\overset{O}{\underset{}{C}}-\overset{CN}{\underset{}{C}}-NOCH_3$$

and/or (O) propamocarb, of the formula $$(CH_3)_2NCH_2-CH_2-CH_2-NHCO-OCH_2CH_3 \quad (XIII)$$

or its hydrochloride and/or (P) fosetyl, of the formula (XIV)

$$CH_3CH_2O-\overset{O}{\underset{H}{\overset{\|}{P}}}-OH$$

or the aluminium adduct thereof and/or (Q) metalaxyl, of the formula (XV)

[chemical structure of metalaxyl]

and/or (R) oxadixyl, of the formula (XVI)

[chemical structure of oxadixyl]

and/or (S) fluazinam, of the formula (XVII)

[Structure: 3-chloro-5-trifluoromethyl-2-pyridinyl linked via NH to 2,6-dinitro-3-chloro-4-trifluoromethylphenyl]

and/or (T) methoxyacrylates, such as methyl (E)-2-{2-[6-(2-cyanophenoxy)pyrimidin-4-yloxy]-phenyl}-3-methoxyacrylate, of the formula (XVIII)

and/or (U) methoximinoacetates, such as methyl (E)-methoximino[α-(o-tolyloxy)-o-tolyl]acetate of the formula (XIX)

and/or (V) furalaxyl +e,dus Λ methyl-N- (2-furoyl) -N- (2,6-xylyl) -alanit and/or (W) azoles of the formula (XX)

I X=Cl, Y=—(CH(OH)—(Triadimenol)

II X = —[phenyl]—, Y = —CH(OH)— (betanol)

III X=Cl, Y=—CO—(triadimefon)

IV tebuconazole of the formula

[Structure of tebuconazole]

and/or (X) etridiazole=3-trichlormethyl-5-ethoxy-1,2,4-thiadiazole and/or (Y) pencycuron=1-(4-chlorbenzyl)-1-cyclopentyl-(3-phenylurea have very good fungicidal properties.

Surprisingly, the fungicidal activity of the active compound combinations according to the invention is substantially greater than the total of the activities of the individual active compounds. This means that a true synergistic effect, which could not have been predicted, is present, not merely a complemented activity.

It can be seen from the structural formula of the active compounds of the formula (I) that the compounds have two asymmetrically substituted carbon atoms. The product can therefore exist in the form of mixture of various isomers or else in the form of a single isomer.

Preferred compounds of the formula (I) are compounds in which the amino acid moiety is formed by ipropyloxycarbonyl-L-valine or sec-butoxycarbonyl-L-valine and the phenethylamine moiety is either racemic or has the S(−) configuration, but in particular the R(+) configuration Particularly preferred compounds of the formula (I) are the compounds in which $R^1$ represents i-propyl.

Particular mention may be made of the compounds 1-methylethyl [2-methyl-1-[[[-1-(4-chlorophenyl)ethyl]-amino]carbonyl]-carbamate, of the formula (II)

(II)

1-Methylethyl [2-methyl-1-[[[1-(4-methylphenyl)ethyl]-amino]carbonyl]-propyl]-carbamate, of the formula (III)

(III)

1-Methylethyl [2-methyl-1-[[[-1-(4-ethylphenyl)ethyl]-amino]carbonyl]-propyl]-carbamate, of the formula (IV)

(IV)

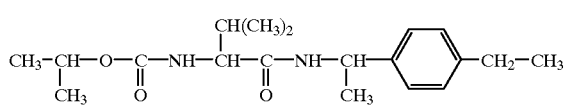

and 1-methylethyl [2-methyl-1-[[[-1- (4-methoxyphenyl)ethyl]amino]carbonyl]-propyl]-carbamate, of the formula (V)

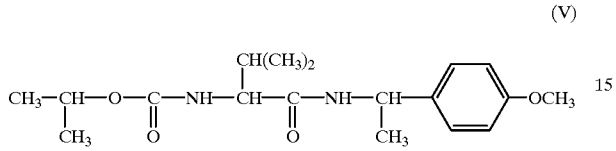

and their isomers, as mentioned above.

The active compounds of the formula (I) are known (cf. EP-A 472,996).

The fungicidal active compounds which are additionally present in the combinations according to the invention are also known. The individual active compounds are described in the following publications:

(A): K. H. Büchel "Pflanzenschutz und Schädlingsbekämpfung" [Crop Protection and Pest Control], page 141, Georg Thieme Verlag, Stuttgart 1977;

(B): K. H. Büchel, loc.cit., page 141 (G) p. 153

(C): K. H. Büchel, loc.cit., page 146 (H) p. 122

(D): K. H. Büchel, loc.cit., page 138 (I) p. 132, 140

(E): K. H. Büchel, loc.cit., page 136 (K) EP-A 219,756

(F): K. H. Büchel, loc.cit., page 137 (L) p. 145

(G): K. H. Büchel, loc.cit., page 153

(H): K. H. Büchel, loc.cit., page 122

(I): K. H. Büchel, loc.cit., page 132

(K): EP-A 219,756

(L): K. H. Büchel, loc.cit., page 145

(M): K. H. Büchel, loc.cit., page 140

(O): DE 1,567,169:*

(P): FR 2,254,276:**

(Q): GB 1,500,581

(R): GB 2,058,059

(S): EP 0 31257

(T): Brighton Crop Protection Conference (1992) 5–6, 435–37

(U): Brighton Crop Protection Conference (1992) 5–6, 403–05

(V): GB 1 448 810

(W): EP-0 040 345, DE 2 324 010, DE 2 201 063

(X): US 3 260 588

(Y): DE 2 732 257.

Besides at least one active compound of the formula (I), the active compound combinations according to the invention comprise at least one active compound from amongst the compounds of groups (A) to (U). In addition, they can also comprise other fungicidally active components which can be admixed.

The synergistic effect is particularly obvious when the active compounds are present in the active compound combinations according to the invention in certain ratios by weight. However, the ratios by weight of the active compounds in the active compound combinations can be varied within a relatively wide range. In general, the following amounts are employed per part by weight of active compound of the formula (I):

1 to 50 parts by weight, preferably 2.5 to 10 parts by weight of active compound from Group (A), 1 to 50 parts by weight, preferably 2.5 to 10 parts by weight of active compound from Group (B), 1 to 50 parts by weight, preferably 1 to 10 parts by weight of active compound from Group (C), 1 to 50 parts by weight, preferably 5 to 20 parts by weight of active compound from Group (D), 1 to 200 parts by weight, preferably 1 to 100 parts by weight of active compound from Group (E), 1 to 50 parts by weight, preferably 5 to 20 parts by weight of active compound from Group (F), 1 to 200 parts by weight, preferably 1 to 100 parts by weight of active compound from Group (G), 1 to 200 parts by weight, preferably 1 to 50 parts by weight of active compound from Group (H), 1 to 100 parts by weight, preferably 1 to 50 parts by weight of active compound from Group (I), 0.5 to 10 parts by weight, preferably 1 to 5 parts by weight of active compound from Group (K), 1 to 50 parts by weight, preferably 1 to 20 parts by weight of active compound from Group (L), 1 to 50 parts by weight, preferably 1 to 20 parts by weight of active compound from Group (M), 0.5 to 20 parts by weight, preferably 1 to 10 parts by weight of active compound from Group (N), 1 to 100 parts by weight, preferably 1 to 50 parts by weight of active compound from Group (O), 1 to 50 parts by weight, preferably 1 to 20 parts by weight of active compound from Group (P), 0.5 to 20 parts by weight, preferably 1 to 10 parts by weight of active compound from Group (Q), 0.5 to 20 parts by weight, preferably 1 to 10 parts by weight of active compound from Group (R), 1 to 20 parts by weight, preferably 1 to 10 parts by weight of active compound from Group (S), 0.5 to 20 parts by weight, preferably 1 to 10 parts by weight of active compound from Group (T)

0.5 to 20 parts by weight, preferably is 1 to 10 parts by weight of active compound from Group (U).

0.5 to 20 parts by weight, preferably 1 to 10 parts by weight of active compound from group (V)

0.5 to 20 parts by weight, preferably 0.5 to 10 parts by weight of active compound from group (W)

0.5 to 20 parts by weight, preferably 0.5 to 10 parts by weight of active compound from group (X), 0.5 to 20 parts by weight, preferably 0.5 to 10 parts by weight of active compound from group (Y)

The active compound combinations according to the invention have very good fungicidal properties and can be employed for combating phytopathogenic fungi, such as, inter alia, Plasmodiophoromycetes, Oomycetes, Chyridiomycetes, Zygomycetes, Ascomycetes, Basidiomycetes and Deuteromycetes.

The active compound combinations according to the invention are particularly suitable for protectively combating Phytophthora infestans and Alternaria spec. on tomatoes and potatoes, as well as Plasmopara viticola on vines.

The good toleration, by plants, of the active compound combinations at the concentrations required for combating plant diseases permits a treatment of above-ground parts of plants, of vegetative propagation stock and seed, and of the soil.

The active compound combinations according to the invention can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds, or active compound combinations with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dye-stuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound or combinations according to the invention can be present in the formulations as a mixture with other known active compounds, such as fungicides, insecticides, acaricides and herbicides, as well as in mixtures with fertilizers or plant growth regulators.

The active compounds can be used as such or in the form of their formulations or the use forms prepared therefrom, such as ready-to-use solutions, emulsifiable concentrates, emulsions, suspensions, wettable powders, soluble powders and granules. They are used in the customary manner, for example by watering, spraying, atomizing, scattering, brushing on in the form of dry seed treatment, as a solution for seed treatment a water-soluble powder for seed treatment or a water-dispersible powder for slurry treatment, or by seed coating.

In the treatment of parts of plants, the active compound concentrations in the use forms can be varied within a relatively wide range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The good fungicidal activity of the active compound combinations according to the invention can be seen from examples. While the individual active compounds have weaknesses in . . . fungicidal activity, the activity of the combinations exceed a simple additive-effect.

Whenever the fungicidal activity of the active compound combinations exceeds the total of the activities of the individually applied active compounds, then the fungicides always show a synergistic effect.

The activity to be expected for a given combination of two active compounds can be calculated as follows (cf. Colby, S. R., "Calculating Synergistic and Antagonistic Responses of Herbicide Combinations", Weeds 15, pages 20–22, 1967):

If x is the degree of effectiveness expressed as a percentage of the untreated control when active compound A is used in a concentration of m ppm, Y is the degree of effectiveness expressed as a percentage of the untreated control when using the active compound B in a concentration of m ppm, and E is the degree of effectiveness expressed as a percentage of the untreated control, which is to be expected when using active compound A and B in a concentration of m and n ppm, then $$E = X + Y - \frac{X - Y}{100}.$$

If the actual fungicidal activity exceeds the calculated value, then the activity of the combination is super-additive, i.e. a synergistic effect exists. In this case, the actually observed degree of effectiveness must exceed the value calculated for the expected degree of effectiveness (E) using the abovementioned formula.

What is claimed is:

1. A fungicidal composition comprising synergistic effective amounts of a valinamide derivative of the formula

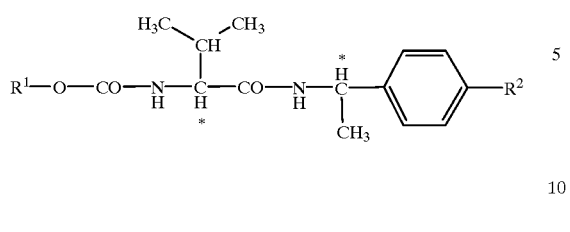 (I)
in which
R¹ represents i-propyl or s-butyl and
R² represents chlorine, methyl, ethyl or methoxy and
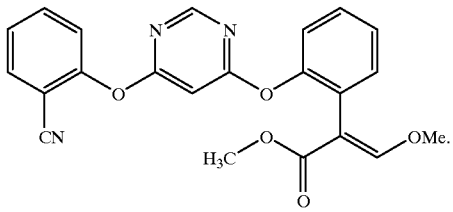 (XVIII)
2. A method of combating fungi which comprises applying such fungi or to a fungus habitat a synergistic fungicidal effective amount of a composition according to claim 1.
* * * * *